(12) United States Patent
Zhang

(10) Patent No.: US 10,920,702 B2
(45) Date of Patent: Feb. 16, 2021

(54) METHOD FOR OPERATING AN ELECTROSTATIC SOOT SENSOR

(71) Applicant: CONTINENTAL AUTOMOTIVE GmbH, Hannover (DE)

(72) Inventor: Hong Zhang, Tegernheim (DE)

(73) Assignee: VITESCO TECHNOLOGIES GMBH, Hannover (DE)

( * ) Notice: Subject to any disclaimer, the term of this patent is extended or adjusted under 35 U.S.C. 154(b) by 237 days.

(21) Appl. No.: 16/063,162

(22) PCT Filed: Nov. 17, 2016

(86) PCT No.: PCT/EP2016/077946
§ 371 (c)(1),
(2) Date: Jun. 15, 2018

(87) PCT Pub. No.: WO2017/102232
PCT Pub. Date: Jun. 22, 2017

(65) Prior Publication Data
US 2019/0024598 A1    Jan. 24, 2019

(30) Foreign Application Priority Data

Dec. 17, 2015 (DE) ..................... 10 2015 225 739.8

(51) Int. Cl.
*G01M 15/10* (2006.01)
*F02D 41/14* (2006.01)
(Continued)

(52) U.S. Cl.
CPC ....... *F02D 41/1466* (2013.01); *G01M 15/102* (2013.01); *G01N 15/0656* (2013.01);
(Continued)

(58) Field of Classification Search
CPC ............ F02D 41/1466; G01M 15/102; G01N 15/0656
(Continued)

(56) References Cited

U.S. PATENT DOCUMENTS

| 2009/0090622 A1* | 4/2009 | Ripley ............... G01N 15/0656 204/401 |
| 2010/0005880 A1 | 1/2010 | Dieterle et al. |

(Continued)

FOREIGN PATENT DOCUMENTS

| DE | 195 36 705 | 4/1997 |
| DE | 10 2006 042 361 | 3/2008 |

(Continued)

*Primary Examiner* — Tarun Sinha
(74) *Attorney, Agent, or Firm* — Cozen O'Connor

(57) ABSTRACT

A method for operating an electrostatic soot sensor by a voltage supply, having a first electrode, a second electrode, and a guard electrode that are electrically insulated from one another. A first electrical potential is applied to the first electrode, and a second electrical potential is applied to the second electrode by the voltage supply, such that a voltage arises between the first and the second electrode. A guard potential is applied to the guard electrode. The measuring current flowing between the first the second electrode is measured with a current-measuring element. In order to determine readiness of the electrostatic soot sensor and with which measuring errors caused by leakage currents can be compensated, to measure leakage currents the first electrode is disconnected from the first electrical potential, and the leakage current flowing between the guard electrode and the second electrode is measured with the current-measuring element.

16 Claims, 3 Drawing Sheets

(51) Int. Cl.
*G01N 15/06* (2006.01)
*G01R 19/00* (2006.01)
G01N 33/00 (2006.01)
G01R 19/165 (2006.01)

(52) U.S. Cl.
CPC ...... *G01R 19/0092* (2013.01); *F01N 2560/02* (2013.01); *G01N 33/0027* (2013.01); *G01R 19/1659* (2013.01)

(58) Field of Classification Search
USPC ....................................................... 73/23.31
See application file for complete search history.

(56) References Cited

U.S. PATENT DOCUMENTS

| | | |
|---|---|---|
| 2014/0144208 A1 | 5/2014 | Allmendinger et al. |
| 2018/0195933 A1* | 7/2018 | Miyagawa ......... G01N 15/0606 |

FOREIGN PATENT DOCUMENTS

| | | |
|---|---|---|
| DE | 10 2007 046 096 | 4/2009 |
| DE | 10 2009 001 064 | 8/2010 |
| EP | 2 511 690 | 10/2012 |

* cited by examiner

METHOD FOR OPERATING AN ELECTROSTATIC SOOT SENSOR

CROSS REFERENCE TO RELATED APPLICATIONS

This is a U.S. national stage of application No. PCT/EP2016/077946, filed on Nov. 17, 2016. Priority is claimed on German Application No. DE 10 2015 225 739.8, filed Dec. 17, 2015, the content of which is incorporated herein by reference.

BACKGROUND OF THE INVENTION

1. Field of the Invention

The invention relates to a method for operating an electrostatic soot sensor.

2. Description of the Prior Art

The reduction of exhaust gas emissions in motor vehicles is an important objective when developing new motor vehicles. Therefore, combustion processes in internal combustion engines are optimized thermodynamically so that the efficiency of the internal combustion engine is significantly improved. In the field of motor vehicles, diesel engines are being increasingly used which, in a modern design, have very high efficiency. The disadvantage of this combustion technology compared to optimized spark ignition engines is, however, a significantly increased emission of soot. Soot has a highly carcinogenic effect as result of the accumulation of polycyclic aromatics, which has already prompted various regulations. For example, exhaust gas emission standards with maximum limits for the emission of soot have been issued. To satisfy the exhaust gas emission standards over a wide area for motor vehicles with diesel engines, there is a need to manufacture cost-effective sensors which reliably measure the soot content in the exhaust gas stream of the motor vehicle.

The use of such soot sensors serves to measure the currently emitted soot so that the engine management system in a motor vehicle can be provided with information in a current driving situation to reduce the emission values through technical control adjustments. Moreover, the soot sensors can be used to initiate active exhaust gas purification by exhaust gas soot filters or exhaust gas recirculation to the internal combustion engine. In the case of soot filtering, filters that can be regenerated filter out a significant part of the soot content from the exhaust gas are used. Soot sensors are required for the detection of soot in order to monitor the function of the soot filters or in order to control their regeneration cycles.

For this purpose, a soot sensor can be connected upstream and/or a soot sensor can be connected downstream of the soot filter, which is also referred to as a diesel particle filter.

The sensor which is connected upstream of the diesel particle filter serves to increase the system reliability and to ensure operation of the diesel particle filter under optimum conditions. Since this depends to a large degree on the quantity of soot trapped in the diesel particle filter, precise measurement of the particle concentration upstream of the diesel particle filter system, in particular the determination of a high particle concentration upstream of the diesel particle filter, is highly significant.

A soot sensor connected downstream of the diesel particle filter provides the possibility of performing vehicle-specific diagnostics and also serves to ensure the correct operation of the exhaust gas after-treatment system.

The state of the art presents various approaches to detecting soot. An approach which is widely adopted in laboratories is to use scattering of light by the soot particles. This procedure is suitable for complex measuring devices. If it is attempted also to use this as a mobile sensor system in the exhaust section it must be borne in mind that approaches from implementing an optical sensor in a motor vehicle entail very high costs. Furthermore, there are unresolved problems with respect to the contamination of the required optical windows by combustion exhaust gases.

DE 195 36 705 A1 discloses a device for measuring soot particles, wherein an electrical field is generated between a cover electrode through which the gas stream flows and an internal electrode within this cover electrode by applying a constant electrical direct voltage, and the charging current for maintaining the constant direct voltage between the cover electrode and the internal electrode is measured. Good measurement results are achieved within the scope of the disclosure in DE 195 36 705 A1 if a direct voltage of 2000 to 3000 V is used to generate the electrical field.

With these electrostatic soot sensors, the current between the two electrodes changes as a function of the soot concentration in the exhaust gas stream. However, the currents occurring here are relatively small and their current strength is of the order of magnitude of nA. Therefore, the entire measuring arrangement must be embodied with very high impedance for these electrostatic soot sensors.

A problem that occurs when measuring soot particles using electrostatic soot sensors in the exhaust section of a motor vehicle is that a cold soot sensor, for example at the start of an internal combustion engine which has cooled down, cannot be used for measuring soot, since condensed water from the exhaust gas stream accumulates on and in the soot sensor and initially makes it unstable for high-voltage operation, which rules out reliable measurement of soot. There is always a high proportion of water in the gas phase in the exhaust gas of an internal combustion engine, since the hydrocarbons, for example from the diesel fuel, mainly burn to form water and carbon dioxide. As long as the soot sensor is cold, the water from the exhaust gas condenses to form liquid water on the electrodes and the insulating body and therefore disrupts the measurement of soot over a long period. Therefore, at the start of the measurement of soot it is necessary to wait until the soot sensor has become so warm that water can no longer condense out of the exhaust gas stream and the water which has already condensed out has dried off from the soot sensor. At this time, what is referred to as the dew point release occurs for the soot sensor. Only very imprecise dew point release can take place exclusively on the basis of engine models in connection with a temperature measurement in the exhaust gas stream, since the complete drying of the soot sensor depends on a very large number of factors (for example ambient temperature of the vehicle, air humidity of the intake air, gas mass flow in the exhaust section). However, even after the drying of the soot sensor, leakage currents can flow via the insulators, which can falsify the measurement results of the soot sensor. Such leakage currents have to be detected in order to be able to correspondingly correct the sensor signal.

SUMMARY OF THE INVENTION

An object of one aspect of the present invention is to specify a method for operating an electrostatic soot sensor with which the readiness of the electrostatic soot sensor for measurement can be determined reliably and precisely and with which measuring errors caused by leakage currents can be compensated.

To measure leakage currents, the first electrode is disconnected from the first electrical potential, and the leakage current flowing between the guard electrode and the second electrode is measured with the current-measuring element, the single current-measuring element can exclusively measure the leakage currents, and therefore determine the readiness of the electrostatic soot sensor for measurement, and in addition measuring errors caused by leakage currents can be compensated.

In one development, the leakage current measured by the current-measuring element is filtered using a low-pass filter. As a result, rapid changes in the leakage current which can be caused, for example, by voltage flashovers are filtered out. These rapid changes in leakage current do not say anything about the general state of the insulating body and they can therefore be filtered out.

In one refinement, the soot sensor is arranged in an exhaust section of an internal combustion engine, and the leakage current is measured when the internal combustion engine has come to a standstill. When the internal combustion engine has come to a standstill, the soot sensor is hot enough to ensure that there is no condensation water on the insulating body, and in addition a measurement of soot is not necessary when the internal combustion engine is stationary. In modern vehicles with start-stop systems, fault current diagnostics would therefore be possible with the method according to the invention whenever the vehicle stops at traffic lights.

Alternatively or in combination with what has been mentioned above, the soot sensor is arranged in an exhaust section of an internal combustion engine, and the leakage current is measured when the internal combustion engine is operating in the overrun cut-off phase.

BRIEF DESCRIPTION OF THE DRAWINGS

In the text which follows, the present invention will be explained with reference to the appended drawings and on the basis of preferred embodiments. These embodiments comprise soot sensors for use in a motor vehicle. In the drawings.

DETAILED DESCRIPTION OF THE PRESENTLY PREFERRED EMBODIMENTS

Figure 1:
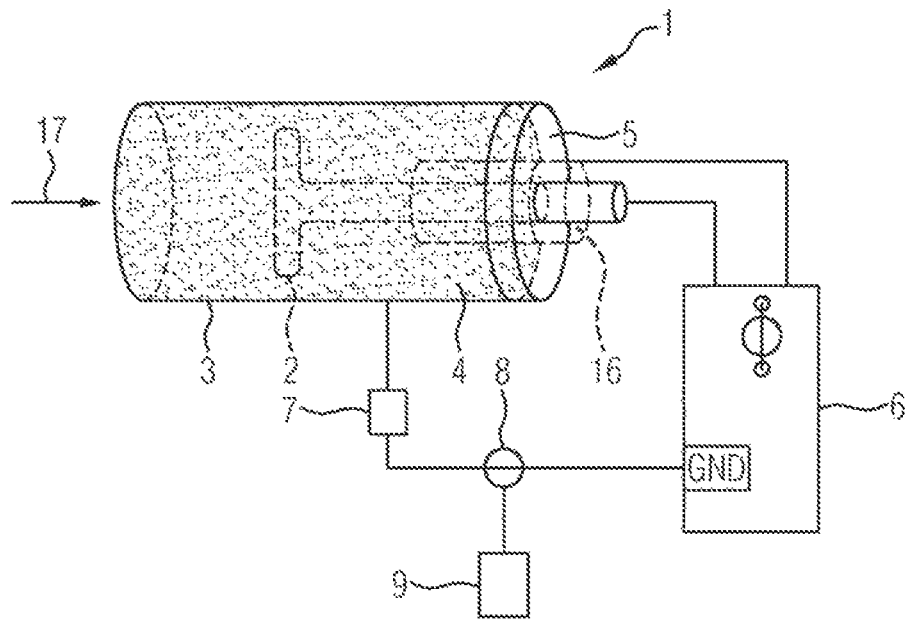
FIG. 1 is a soot sensor.

FIG. 1 shows a soot sensor 1. The soot sensor 1 comprises a first electrode 2 arranged in the interior of a second electrode 3. The exhaust gas 17 of the internal combustion engine 51 in which soot particles 4 are contained is located between the first electrode 2 and the second electrode 3. The concentration of the soot particles 4 in the exhaust gas 17 is measured by the soot sensor 1. In other words, it is possible to say that the soot content in the exhaust gas stream 17 is to be determined by means of the soot sensor 1.

A measuring voltage is applied between the first electrode 2 and the second electrode 3 by the voltage supply 6. This voltage results from a first electrical potential 14 applied to the first electrode and a second electrical potential 18 applied to the second electrode 3. The first electrode 2 is electrically insulated from the second electrode 3 using the insulating body 5. The insulating body 5 can be embodied, for example, as a disk made of a ceramic material. Moreover, a guard electrode 16 is arranged in the soot sensor 1. The guard electrode 16 is used primarily to stabilise the voltage conditions and electrical potentials in the soot sensor ensuring that no leakage currents flow between the first electrode 2 and the second electrode 3 during the measuring operation of the soot sensor 1.

Leakage currents are undesired currents which flow through the insulating body 5 during the measuring operation of the soot sensor 1 as a result of insufficient insulation properties, and therefore falsify the measurement results of the soot sensor 1 significantly.

During the soot-measuring operation, the guard potential 19 applied to the guard electrode 16 is set somewhat above the second electrical potential present at the second electrode 3, but far below the first electrical potential 14 present at the first electrode 2. As a result, possibly present leakage currents flow to the guard electrode 16 and are diverted there, without influencing the measurement of the current of the soot sensor 1. In a typical measuring configuration, the second electrode 3 is at ground potential GND, that is to say at 0 V, the guard electric 16 is a somewhat increased potential, for example at 0.5 V to 1 V, and the first electrode is a very high potential, for example 1000 V.

Furthermore, it is apparent in FIG. 1 that an ohmic resistor 7, which is embodied with high impedance in order to measure the relatively small currents formed owing to the soot particles 4 between the first electrode 2 and the second electrode 3, is connected between the voltage supply and the second electrode 3. The measuring of these currents is carried out by the current-measuring element 8 connected to evaluation electronics 9. Such soot sensors 1 are used for on-board diagnostics in motor vehicles with diesel engines.

The voltage applied between the first electrode 2 and the second electrode 3 is relatively high, in order to obtain usable measuring currents. Such a voltage is between 100 V and 3 kV, and is therefore relatively laborious to control.

In particular, accumulations of water on the first electrode 2 and the second electrode 3, as well as on the insulating body 5, can bring about complete falsification of the soot measurement. Therefore, the soot sensor 1 must be completely dried before the start of the soot measurement, which is signalled by what is referred to as the dew point release. However, deterioration of the insulation properties of the insulating body can also worsen the measurement results. This degradation can go so far that the soot sensor 1 is unusable for diagnostics of the soot particle filter and has to be replaced, or at least the diagnostics of the soot particle filter are severely falsified.

Figure 2:
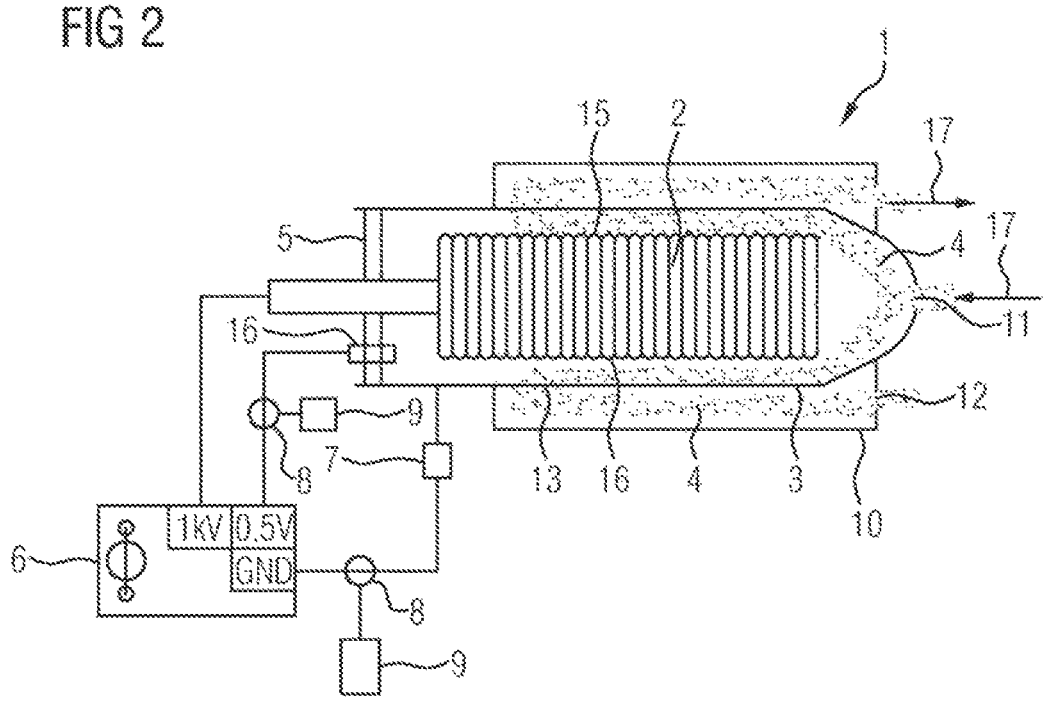
FIG. 2 is a further soot sensor.

FIG. 2 shows a soot sensor 1 with a first electrode 2 and a second electrode 3. The first electrode 2 is electrically insulated from the second electrode 3 by an insulating body 5. An electrical voltage of 1 kV, generated by the electrical voltage supply 6, is applied between the first electrode 2 and the second electrode 3.

Soot particles 4 transported through an exhaust section 49 in an exhaust gas stream of an internal combustion engine 51 can penetrate the soot sensor 1, which is integrated into the exhaust section 49. The soot particles 4 enter an electrical field formed between the first electrode 2 and the second electrode 3 owing to the applied electrical voltage. To generate an electrical current that can be measured between the first electrode 2 and the second electrode 3, elements 15 for concentrating the electrical field strength can be formed on the surface of the first electrode 2 and/or on the surface of the second electrode 3. In this example, the first electrode 2 is embodied as a bar-shaped threaded rod, wherein the elements 15 are designed to concentrate electrical field strength through the threads, between which triangular peaks are formed. The electrical field is concentrated at these peaks, as a result of which the electrical field strength in the region of the peaks becomes very high. The pronounced increase in the electrical field strength in the region of the peaks can exceed the breakdown field strength of the gas in the region. When the breakdown field strength of the gas is exceeded, electrically charged particles are formed which are accelerated in the direction of the opposite electrode, and owing to impact ionizations give rise to an avalanche-like formation of charge carriers. If this charge carrier avalanche reaches an electrode surface, very high current can be measured which can be evaluated and which is proportional to the number of the charged particles in the exhaust gas.

FIG. 2 also shows an ohmic resistor 7, which is advantageous for being able to use the evaluation electronics 9 to measure the electrical current which flows between the first electrode 2 and the second electrode 3. Moreover, FIG. 2 shows a protective cap 10 that serves to guide the exhaust gas stream 17 through the soot sensor 1 in a targeted fashion. The exhaust gases can, for example, penetrate the soot sensor 1 through a first opening 11, where the soot content in the exhaust gas can be measured between the first electrode 2 and the second electrode 3. After this, the exhaust gas stream 17 exits the soot sensor 1 through the second opening 12 formed in the second electrode 3, and is fed back into the main exhaust gas stream via the third opening 13.

A guard electrode 16 can be seen in the insulating body 5. The guard electrode 16 can be used to measure, before the time of the dew point release, a current that serves as an indicator for a dew point release of the soot sensor 1. The current is driven via the moist insulating body to the guard electrode 16 by the voltage at the first electrode 2 (in this example 1 kV), the guard electrode 16 being biased in this example with 0.5 V somewhat towards the ground potential GND at the second electrode 3. Complete drying of the soot sensor 1 can be inferred only when this current drops clearly, this is so by at least one power of ten, after the start of the cold internal combustion engine and a dew point release can take place. However, with this type of dew point release at least two current measuring elements 8, specifically one in the line between the guard electrode 16 and the voltage supply 6 and one in the line between the first or second electrode 2, 3 and the voltage supply 6, are necessary to operate the soot sensor 1. The number of necessary current-measuring elements 8 increases the cost of the soot sensor 1. However, it is any case advantageous to keep the manufacturing costs for the soot sensor 1 as low as possible.

However, it is also conceivable to use a current measurement between the first electrode 2 and the second electrode 3, that is to say between 1 kV and the ground potential GND, in order to determine the time of the dew point release. The dropping of the current by at least one power of ten is also evaluated here as a sign of complete drying of the soot sensor after the start of the cold internal combustion engine.

Figure 3:
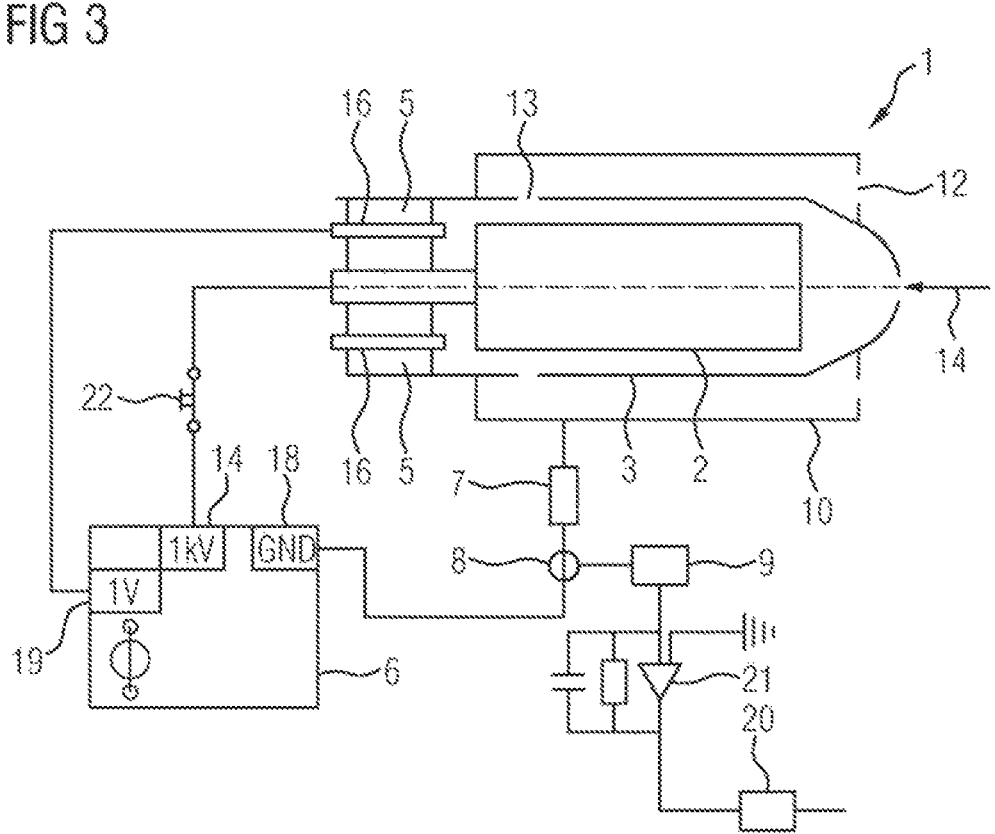
FIG. 3 is a soot sensor that is operated with the method according one aspect of to the invention.

FIG. 3 shows a soot sensor 1 with a voltage supply 6 that can be operated with the method according to the invention. The soot sensor 1 has a first electrode 2 and a second electrode 3. The soot particles can penetrate the interior of the soot sensor with the exhaust gas stream 17 through a first opening 11 formed in the protective cap 10. In this context, the soot particles enter the intermediate space between the first electrode 2 and the second electrode 3. Furthermore, the soot sensor 1 has a voltage supply 6. Using a switching element 22, the first electrode 2 can be disconnected from the first potential 14 and connected, for example, to the ground potential (GND). The ground potential GND is formed by the electrical ground of the motor vehicle 50. The guard potential 19 applied to the guard electrode 6 by the voltage supply 6 can be, for example, 0.5 V to 1 V to GND. The first potential 14 applied to the first electrode 2 during the soot measurement can be, for example, 1000 V to the ground potential GND.

As long as the exhaust gas sensor 1 is cold, which will be the case e.g. after the new start of the internal combustion engine, water molecules present in the gas stream 17 are deposited as condensate in the entire soot sensor 1. This water condensate settles inter alia on the insulating body 5, wherein an electrically conductive connection is produced between the first electrode 2, the guard electrode 16, and the second electrode 3. The leakage current that flows through the insulating body 5 into the aqueous condensate, makes measurement of the soot with the wetted soot sensor 1 impossible. Nevertheless, this current can be observed to detect the dew point release of the soot sensor 1 and to initiate the measurement phase of the soot sensor 1. After the dew point release, that is to say in the measuring phase of the soot sensor 1, the remaining leakage currents that flow through the insulating body 5 can be measured with the method according to the invention and compensated. In this context, in order to measure the remaining leakage currents, the first electrode 2 is disconnected from the first electrical potential 14 using the switching element 22, and the leakage current flowing between the guard electrode 16 and the second electrode 3 is measured by the current-measuring element 8. The leakage current measured by the current-measuring element 8 can be filtered using a low-pass filter 21. The values of the measured leakage current can be stored in a memory element 20, and the soot sensor is identified as faulty if the value of the leakage current exceeds a previously defined limiting value.

To precisely determine the soot content in the exhaust gas of the internal combustion engine 51, the previously determined leakage current can be subtracted from the measured measuring current. This is a fault correction, in order to be able to determine the soot content in the exhaust gas stream of the internal combustion engine safely and accurately.

If the soot sensor 1 is used to diagnose a soot particle filter 52, and the soot sensor 1 detects a defect in the soot particle filter 52, this signal can also originate from a leakage current in the soot sensor 1. It is therefore appropriate after the detection of a defect in the soot particle filter 52 to perform measurement of the leakage current in the soot sensor 1 once more, in order to avoid an incorrect defect diagnosis of the soot particle filter 52.

Figure 4:
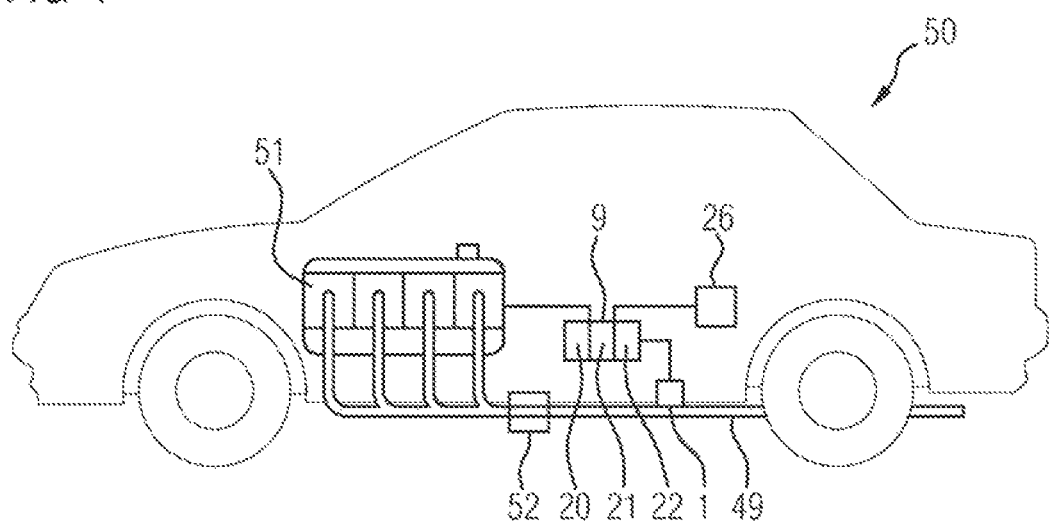
FIG. 4 is a motor vehicle having an internal combustion engine.

FIG. 4 shows a motor vehicle 50 having an internal combustion engine 51 and an exhaust section 49. A soot particle filter 52 and a soot sensor 1 are arranged in the exhaust section. The soot sensor 1 is connected to evaluation electronics 9 which can contain, for example, a memory element 20, a low-pass filter 21 and/or a switching element 22. The switching element 22 is generally embodied as an electronic switch. In addition, FIG. 4 also shows an on-board diagnostic unit 26 that can store, for example, a detected faulty state of the soot sensor.

Figure 5:
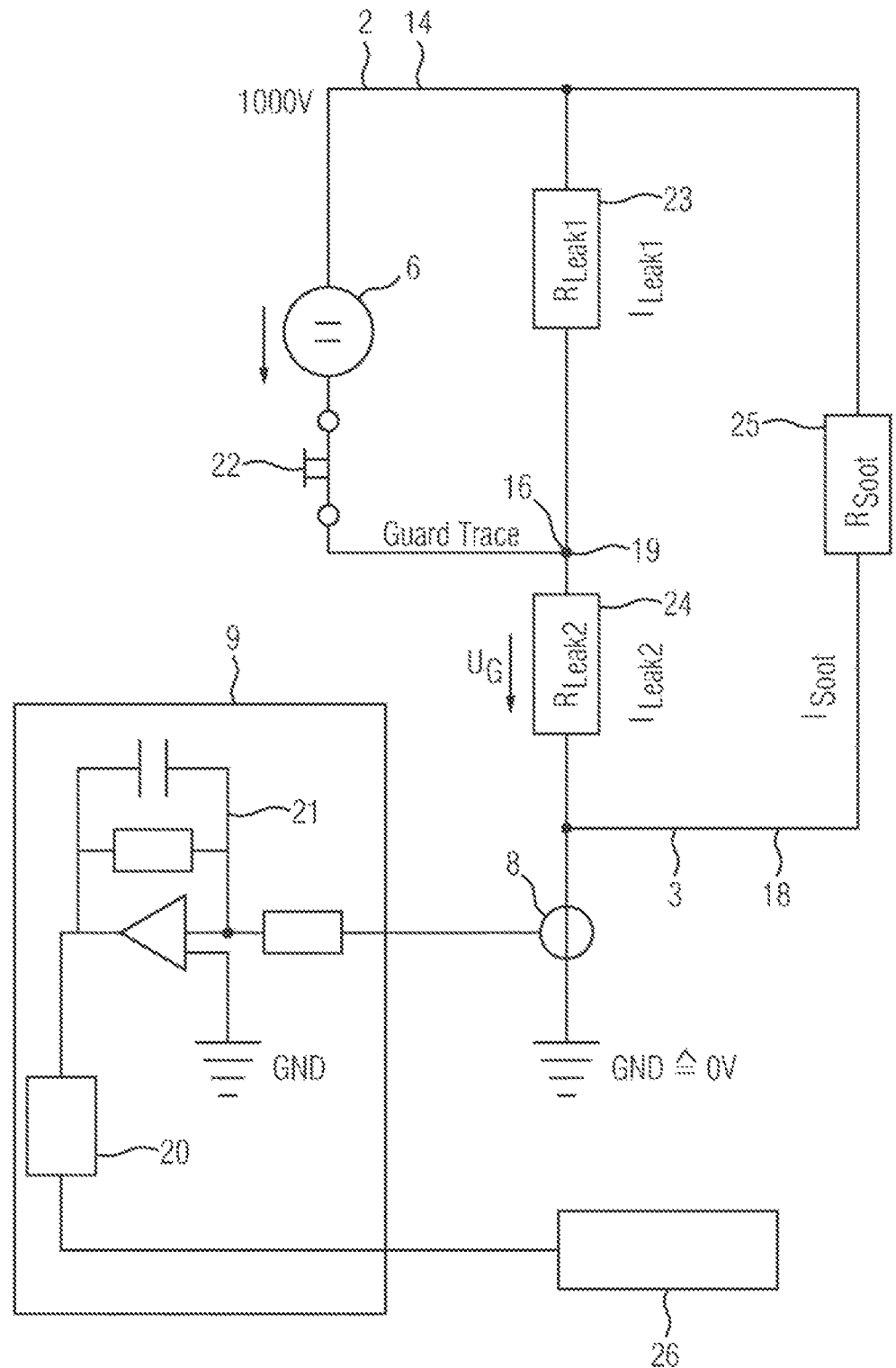
FIG. 5 is an equivalent circuit diagram of the electrostatic soot sensor.

FIG. 5 shows an equivalent circuit diagram of the soot sensor 1 that can be operated with the method according to the invention. The soot sensor 1 is connected to a voltage supply 6. The voltage supply 6 applies a maximum voltage of 1000 V to the first electrode 14 and the ground potential GND to the second electrode. The guard electrode 16 is supplied with the guard potential 19 (for example 1 V). In the measuring phase of the soot sensor 1, the current Isoot flows via the third equivalent resistor 25 and can be measured by the single current-measuring element 8 or a further current-measuring element, and this measurement result can be further processed by the evaluation electronics 9. The first electrode 2 can be disconnected from the first potential 14 by the switching element 22. In addition, after the disconnection of the first electrode 2 from the first potential 14, the switching element 22 can connect the first electrode 2 to the ground potential GND. The leakage current Ileak1 and/or the leakage current Ileak2 are then driven by the guard potential 19 via the first equivalent resistor 23 and/or the second equivalent resistor 24 and measured by the current-measuring element 8. The measured values for the leakage current can be filtered by a low-pass filter 21 and stored in a memory element 20. The measured values for the leakage current can be retrieved from the memory element 20 and used to correct the measured values for the quantity of soot. Moreover, a signal can be sent to the on-board diagnostic unit 26 if the values for the leakage current exceed a previously determined threshold. The soot sensor 1 can then be categorized as defective in the on-board diagnostic unit 26.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for operating an electrostatic soot sensor by means of a voltage supply, wherein the electrostatic soot sensor has a first electrode, a second electrode, and a guard electrode, wherein the first electrode and the second electrode are electrically insulated from one another by an insulating body, and the guard electrode is arranged between the first electrode and the second electrode, wherein the guard electrode is electrically insulated from the first electrode and the second electrode by the insulating body, the method comprising:

determining a dew point release;

applying a first electrical potential is applied to the first electrode by the voltage supply;

applying a second electrical potential to the second electrode by the voltage supply such that an electrical voltage arises between the first electrode and the second electrode;

applying a guard potential to the guard electrode by the voltage supply, wherein the applied guard potential is greater than the second electrical potential;

measuring a measuring current flowing between the first electrode and the second electrode with a current-measuring element;

disconnecting the first electrode from the first electrical potential to measure a leakage current flowing between the guard electrode and the second electrode; and measuring the leakage current flowing between the guard electrode and the second electrode with the current-measuring element.

2. The method for operating an electrostatic soot sensor as claimed in claim 1, further comprising:

filtering the leakage current measured by the current-measuring element using a low-pass filter.

3. The method for operating an electrostatic soot sensor as claimed in claim 1, wherein the electrostatic soot sensor is arranged in an exhaust section of an internal combustion engine, and the leakage current is measured when the internal combustion engine has come to a standstill.

4. The method for operating an electrostatic soot sensor as claimed in claim 1, wherein the electrostatic soot sensor is arranged in an exhaust section of an internal combustion engine, and the leakage current is measured when the internal combustion engine is operating in an overrun cut-off phase.

5. The method for operating an electrostatic soot sensor as claimed claim 1, further comprising:

determining a soot content in an exhaust gas of an internal combustion engine by subtracting the leakage current from the measured measuring current.

6. The method for operating an electrostatic soot sensor as claimed in claim 1, further comprising:

measuring a plurality of values of the leakage current;

storing the plurality of values of the leakage current in a memory element; and identifying the electrostatic soot sensor as faulty if a value of the leakage current exceeds a previously defined limiting value.

7. The method for operating an electrostatic soot sensor as claimed in claim 1, wherein the first electrode is connected to a ground potential (GND) after the first electrode has been disconnected from the first electrical potential.

8. The method for operating an electrostatic soot sensor as claimed in claim 2, wherein the electrostatic soot sensor is arranged in an exhaust section of an internal combustion engine, and the leakage current is measured when the internal combustion engine has come to a standstill.

9. The method for operating an electrostatic soot sensor as claimed in claim 1, wherein the guard electrode stabilises the electrical potentials to ensure that no leakage currents flow between the first electrode and the second electrode during the measuring operation.

10. The method for operating an electrostatic soot sensor as claimed in claim 1, wherein the guard potential applied to the guard electrode is 0.5 V to 1 V.

11. The method for operating an electrostatic soot sensor as claimed in claim 1, wherein the guard potential is greater than a ground potential (GND).

12. The method for operating an electrostatic soot sensor as claimed in claim 6, further comprising:

repeating the measuring of the plurality of values of the leakage current to confirm that the electrostatic soot sensor as faulty.

13. The method for operating an electrostatic soot sensor as claimed in claim 1, wherein the dew point release is measured using the guard electrode, wherein a current is an indicator for the dew point release.

14. The method for operating an electrostatic soot sensor as claimed in claim 13,
- wherein the current is driven via a moist insulating body to the guard electrode by a 1 kV voltage at the first electrode,
- wherein a drying of the soot sensor is determined when this current drops by at least one power of ten after a start of the cold internal combustion engine.

15. The method for operating an electrostatic soot sensor as claimed in claim 1, wherein the dew point release is determined by a current measurement between the first electrode 2 and the second electrode.

16. The method for operating an electrostatic soot sensor as claimed in claim 15,
- wherein the current is driven via a moist insulating body to the guard electrode by a 1 kV voltage at the first electrode,
- wherein a drying of the soot sensor is determined when this current drops by at least one power of ten after a start of the cold internal combustion engine.

\* \* \* \* \*